United States Patent [19]
Suzuki et al.

[11] Patent Number: 4,549,206
[45] Date of Patent: Oct. 22, 1985

[54] METHOD AND APPARATUS FOR EXAMINING PRINTED CIRCUIT BOARD PROVIDED WITH MINIATURIZED ELECTRONIC PARTS

[75] Inventors: Etsuji Suzuki, Tokyo; Shinichi Uno, Kawasaki; Kiyomu Chiyoda, Ayase; Ryuhachirou Douji, Yokohama, all of Japan

[73] Assignee: Tokyo Shibaura Denki Kabushiki Kaisha, Tokyo, Japan

[21] Appl. No.: 434,924

[22] Filed: Oct. 18, 1982

[30] Foreign Application Priority Data

Oct. 19, 1981 [JP] Japan ................. 56-165707

[51] Int. Cl.4 ............................. H04N 7/18
[52] U.S. Cl. ................. 358/106; 356/239; 250/563; 382/8
[58] Field of Search .............. 382/8, 48, 45; 358/106, 358/93, 96, 107; 356/239, 394, 237; 250/562, 563

[56] References Cited

U.S. PATENT DOCUMENTS 3,688,235 6/1976 Migeotte ................. 356/239
3,813,173 5/1974 Teter ....................... 356/239
3,963,354 6/1976 Feldman et al. ......... 356/239
4,115,802 9/1978 Kramer et al. ........... 358/106
4,342,515 8/1982 Akiba et al. .............. 356/239
4,449,818 5/1984 Yamaguchi et al. ...... 358/106

FOREIGN PATENT DOCUMENTS 2104649 7/1982 United Kingdom .
2047879 8/1983 United Kingdom .

OTHER PUBLICATIONS

UK Patent Office Action-Jun. 11, 1984.

Primary Examiner—Edward L. Coles, Sr.
Attorney, Agent, or Firm—Cushman, Darby & Cushman

[57] ABSTRACT

The rear and front surfaces of a printed circuit board are illuminated by parallel light beams from first and second illuminating systems, respectively. The obtained transmitted light and reflected light are received by an image sensor through a lens system to provide video data which is stored in a video memory. Abrasion scars are formed by brushing the surfaces of terminals formed on the front surface of the printed circuit board prior to soldering. The presence or absence of a chip element is discriminated by a microprocessor in accordance with the difference between reflection factors of light emitted by the second illuminating system and reflected from the terminals and light reflected from the chip element.

16 Claims, 4 Drawing Figures

METHOD AND APPARATUS FOR EXAMINING PRINTED CIRCUIT BOARD PROVIDED WITH MINIATURIZED ELECTRONIC PARTS

BACKGROUND OF THE INVENTION

The present invention relates to a method and an apparatus for examining if a miniaturized electronic part is correctly mounted in a predetermined position on a printed circuit board or the like.

Miniaturized electronic parts or microparts so-called chip elements are widely used nowadays in place of electronic parts with lead wires. Such a chip element is frequently mounted on a printed circuit board together with electronic parts with lead wires. During assembly of a circuit, chip elements are temporarily adhered in predetermined positions on a printed circuit board with an adhesive, hardened in a drying furnace, and soldered. Temporary adhesion of the chip element onto the printed circuit board is performed on an automatic manufacturing line for mass-producing printed circuit boards.

However, when the chip elements are temporarily adhered on the printed circuit board, the chip elements may become misaligned from their correct positions or separated from the printed circuit board, or may be adhered at wrong positions on the printed circuit board. If such an error is found after soldering, much labor is required to correct it, resulting in higher manufacturing cost or a lower yield of the printed circuit boards. For this reason, it is very important to identify before soldering any adhesion of the chip elements at erroneous positions or separation of the chip elements, and to correct the same.

Misalignment or separation of chip elements after adhesion are conventionally identified by visual observation which requires much labor and is inefficient and unreliable.

It is also proposed to process image data of a printed circuit board having chip elements mounted thereon, where the data is obtained by an image pickup camera, so as to examine misalignment or separation of the chip elements. However, correct examination is still difficult by this method due to misalignment of the printed circuit board during examination, or warp or distortion of the printed circuit board. The surface of a printed circuit board on which the chip elements are mounted also has a printed wiring pattern of copper foil or printed characters formed thereon. For this reason, a highly complex pattern recognition technique of image data is required to identify the chip elements from such patterns. Such a highly complex pattern recognition technique is also subject to examination errors.

SUMMARY OF THE INVENTION

It is an object of the present invention to provide a method and an apparatus for allowing easy and reliable examination of chip elements mounted on a printed circuit board.

In order to achieve this object, there is provided a method and an apparatus for examining a printed circuit board, which utilize the fact that, when a chip element is mounted on a printed circuit board having some degree of transparency, the combined level of reflected light of light obliquely incident on the surface of the printed circuit board, on which the chip element is mounted in the direction perpendicular to the abrading direction of printed conductors, together with transmitted light through the printed circuit board, becomes extremely low at the portion of the chip element.

DETAILED DESCRIPTION OF THE PREFERRED EMBODIMENT

Figure 1:
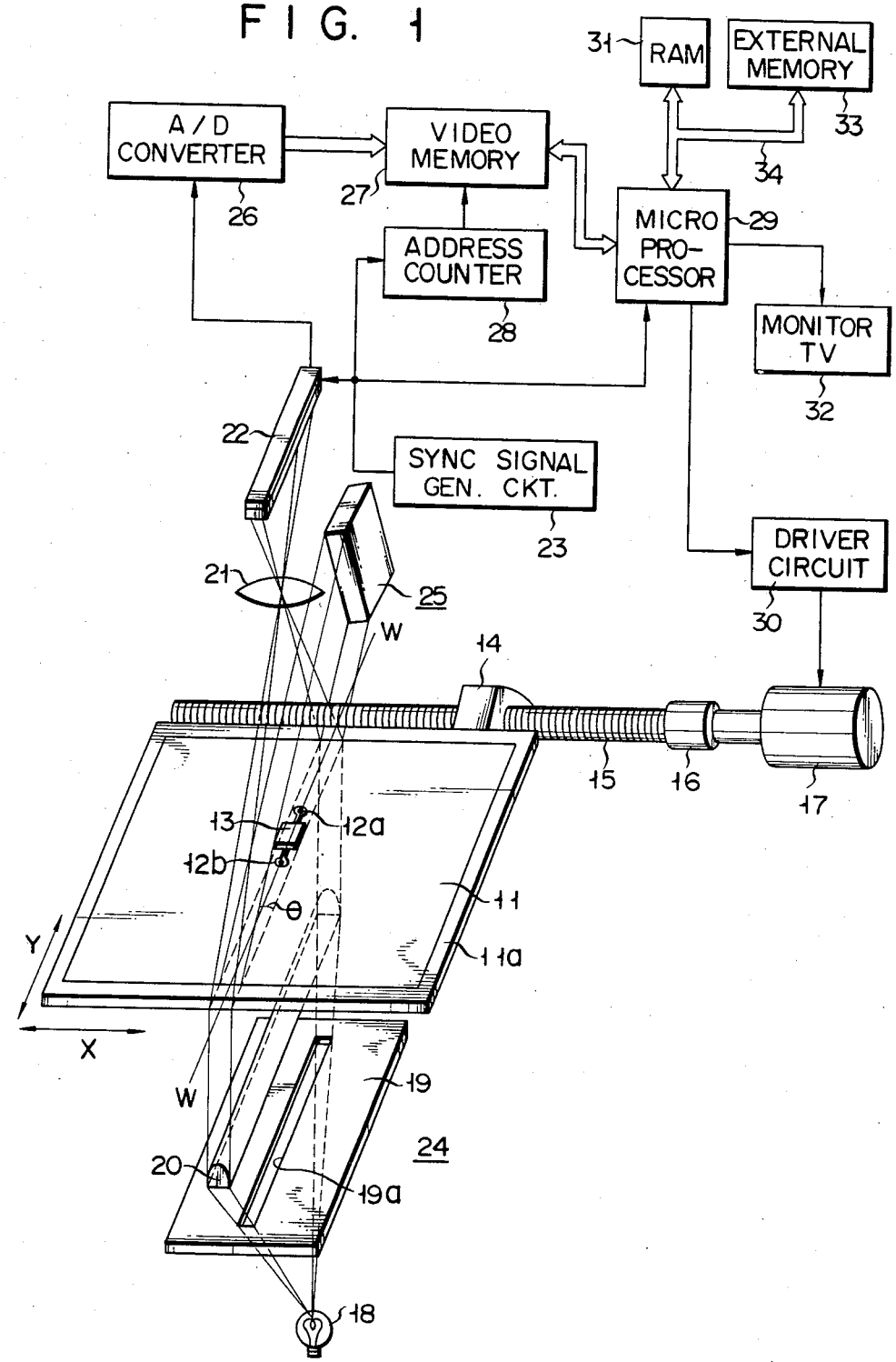
FIG. 1 is an overall view of an apparatus according to an embodiment of the present invention including a block diagram thereof.

The preferred embodiment of the present invention will now be described in detail with reference to the accompanying drawings. In FIG. 1 there is shown a printed circuit board 11 which is a semitransparent insulating plate of an epoxy resin or the like and which is held by a frame 11a. Printed wiring terminals 12a and 12b made of printed conductors are formed on one surface of the printed circuit board 11. A chip element 13 such as a semiconductor element or a resistor element is temporarily adhered with an adhesive between these conductors 12a and 12b.

The frame 11a is fixed with a nut 14 which is, in turn, threadably engaged with a feed screw 15. The feed screw 15 is coupled to the rotating shaft of a pulse motor 17 through a coupling 16. Upon rotation of the pulse motor 17, the nut 14 and hence the frame 11a is moved in the direction indicated by arrow X. A direction perpendicular to the direction X is indicated by reference symbol Y.

The printed circuit board 11 is illuminated by a lamp 18 from below along its entire length in the Y direction from its one end to its other end. Light from the lamp 18 becomes incident on a cylindrical lens 20 through a thin slit 19a formed in a slit plate 19. The cylindrical lens 20 serves to convert the incident light into parallel light beams which vertically illuminate the rear surface of the printed circuit board 11.

Since the terminals 12a and 12b are formed by copper foil, they do not transmit any portion of light and nor does the chip element 13 transmit light. On the other hand, since the printed circuit board 11 is semitransparent, the images of the terminals 12a and 12b and the chip element 13 are formed on an image sensor 22 through a lens system 21. Although the lens system 21 in the figure comprises a convex lens alone for the sake of simplicity, it is actually a combination of a plurality of lenses. The image sensor 22 comprises a photodiode array, a CCD image pickup device or the like. The image from one end to the other end of the printed circuit board 11 along the Y direction is received as one-line image data and is converted into electrical signals. Clock signals generated by a sync signal generating circuit 23 are supplied to the image sensor 22 so as to perform line scanning at a predetermined speed.

The lamp 18, the slit plate 19, and the cylindrical lens 20 make up a first illuminating system 24 which illuminates the rear surface of the printed circuit board 11. In addition to this, a second illuminating system 25 is provided for illuminating the front surface of the printed circuit board 11, that is, the surface of the printed circuit board 11 on which the chip element 13 is mounted. Since the configuration of the second illuminating system 25 is the same as that of the first illuminating system, it is only indicated with a block in the figure for the sake of simplicity. The second illuminating system 25 radiates parallel light beams which have an angle θ with respect to the front surface of the printed circuit board 11 and which illuminate the part of the printed circuit board 11 along the Y direction which is illuminated by the first illuminating system 24. These parallel light beams are reflected by the surface of the printed circuit board 11, and reflected light beams carrying the surface image data are focused on the image sensor 22 through the lens 21 to form an image thereon.

Image signals from the image sensor 22 are converted into digital video data by an A/D converter 26 which is then supplied to a video memory 27. The video memory 27 has, for example, 2,048×64 memory locations which are designated by addresses generated by an address counter 28 counting the clock signals of the circuit 23 supplied to the image sensor 22. Video data obtained by the one-line scanning operation of the image sensor 22 is stored after being divided into 64 unit data pieces in correspondence with the portion along the Y direction of the printed circuit board 11 on which the chip element 13 is mounted.

The clock signals from the sync signal generating circuit 23 are also supplied to a microprocessor 29 to supply a drive pulse to a driver circuit 30 every time the video data of one line is stored in the video memory 27. In response to the drive pulse, the driver circuit drives the pulse motor 17. Then, the printed circuit board 11 is moved in the X direction by a predetermined distance. When the printed circuit board 11 completes its movement from its one end to its other end with respect to the first and second illuminating systems 24 and 25, the video data which is a combination of the transmitted light image and the reflected light image of the entire surface of the printed circuit board 11 is stored in the video memory 27.

The video data stored in the video memory 27 is supplied to a RAM 31 and a monitor TV 32 through the microprocessor 29. An external memory such as a floppy disk device 33 is further coupled to the microprocessor 29 through a bus line 34. The floppy disk device 33 prestores data of the positions of the terminals 12a and 12b on the printed circuit board 11 and chip elements 13 mounted between the terminals 12a and 12b. For the sake of simplicity, FIG. 1 shows only one pair or terminals 12a and 12b and one chip element 13. However, in practice, a plurality of pairs of terminals are formed on the printed circuit board. In this embodiment, circular through holes are respectively formed in the terminals 12a and 12b and the printed circuit board 11, so that light of highest intensity transmitted therethrough may reach the image sensor 22.

Figure 2:
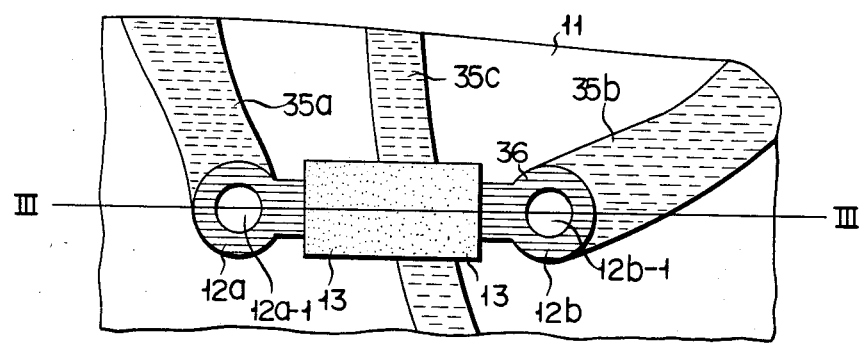
FIG. 2 is a plan view of part of a printed circuit board having a chip element mounted thereon.
Figure 3:
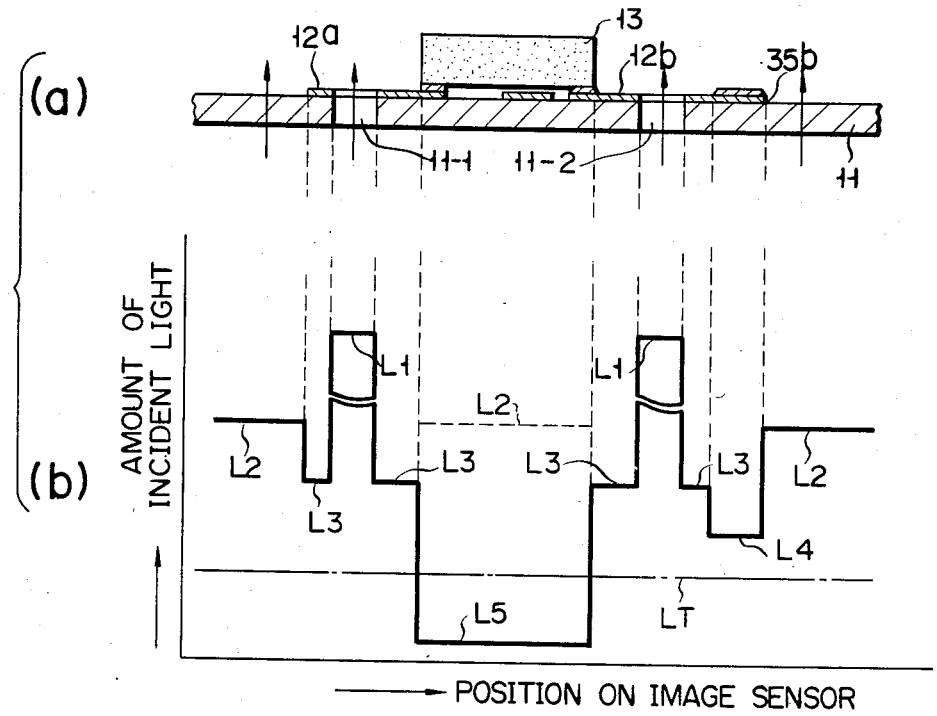
FIG. 3 shows a sectional view of the board shown in FIG. 2 along the line III—III therein and a chart showing an amount of incident light on an image sensor shown in FIG. 1.

As shown in FIGS. 2 and 3, circular through holes 12a-1 and 12b-1 are formed in the bulged portions of the terminals 12a and 12b, respectively. Similar through holes 11-1 and 11-2 are formed in the printed circuit board 11 in correspondence with these through holes 12a-1 and 12b-1, respectively. The chip element 13 of rectangular shape is mounted between the ends of the terminals 12a and 12b. The chip element 13 is coated with a black or dark brown paint and has an extremely low transmission factor and reflection factor. Therefore, when the light from the first illuminating system 24 illuminates the rear surface of the printed circuit board 11, the light which reaches the image sensor 22 through the through holes 11-1, 11-2, 12a-1 and 12b-1 has a highest intensity, as shown in FIG. 3. A light intensity level of the image sensor 22 corresponding to these holes is indicated by L1. Level L1 does not include light radiated from the second illuminating system 25.

Before mounting the chip element 13, abrasion scars 36 of a uniform direction are formed by brushing the surfaces of terminals 12a and 12b. Brushing is performed so as to improve solderability of the chip element 13 and the terminals 12a and 12b. The abrasion scars 36 are formed along the X direction in FIG. 1. Then, the light from the second illuminating system 25 illuminates the printed circuit board 11 perpendicular to the direction of the abrasion scars 36. The incident angle of the light emitted from the second illumination system 25 may preferably be set in such a manner that the amount of light received by the image sensor 22, which is reflected from the portion of the abrasion scars 36 becomes maximum.

Figure 4:
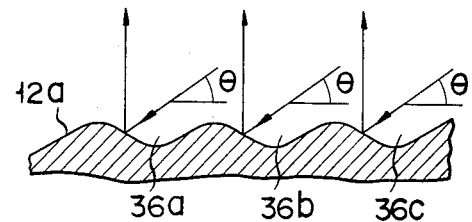
FIG. 4 is a sectional view for explaining the manner in which light from a light source at the side of the front surface of the printed circuit board shown in FIG. 1 is reflected by the surface of an abraded portion of a printed conductor provided on the board.

Brushing is performed, for example, by abrading the surface of the printed circuit board 11 with a wire brush. The abrasion scars 36 formed in this manner are as shown enlarged in FIG. 4. Although the abrasion scars 36 may not in practice be formed as regularly as shown in FIG. 4, they may be considered to be formed as shown in this figure from a statistical viewpoint. FIG. 4 shows the surface of the terminal 12a as an example. Light from the second illuminating system 25 is reflected at the inclined side surfaces of the abrasion scars 36a to 36c and becomes incident on the image sensor 22 through the lens system 21.

In the case where the conductors are not formed on the printed circuit board 11, the intensity level of the incident light on the image sensor 22 is L2, which is lower than L1 given by the transmitted light through holes from the first illuminating system 24.

The terminals 12a and 12b do not substantially transmit light from the first illuminating system 24. However, due to the light reflected by the second illuminating system 25, the intensity level of the incident light on the image sensor 22 corresponding to the terminals 12a and 12b becomes L3, which is lower than L2.

The printed conductor 35b does not substantially transmit light from the first illuminating system 24 as in the case of the terminals 12a and 12b. Furthermore, the light from the second illuminating system 25 is only slightly reflected from its surface coated with transparent resist, so that the intensity level of the incident light on the image sensor 22 corresponding to it is L4, which is lower than L3.

Since the chip element 13 is printed black and has a satin finish, it does not transmit light from the first illuminating system 24 at all, and does not reflect light from the second illuminating system 25. Therefore, the intensity level of the incident light on the image sensor 22 corresponding to the chip element 13 is L5, which is even lower than L4.

If the chip element 13 is not mounted between the terminals 12a and 12b, the intensity level of the incident light on the image sensor 22 corresponding to the chip element 13 becomes L2 except for that corresponding to the conductor 35c (see FIG. 3), which is the same as that of the remaining portions of the printed circuit board 11. However, if the chip element 13 is mounted, the intensity level is L5, providing a large difference in intensity from L2. Therefore, the microprocessor 29 can easily detect if a chip element 13 is mounted between the terminals 12a and 12b in the following manner. The positions of the terminals 12a and 12b are read at level L1 in correspondence with the imaginary checking line W—W shown in FIG. 1 (corresponding to the line III—III in FIG. 2). Taking these positions as a reference, a threshold level LT is set between levels L4 and L5. If the microprocessor 29 detects the presence of the chip element 13 from the data stored in the RAM 31, it reads out the corresponding data from the floppy disk device 33 and compares it with the data from the RAM 31. If the data read out from the floppy disk device 33 indicates the presence of the chip element 13 between the terminals 12a and 12b, the chip element 13 is confirmed to have been correctly mounted. The data stored in the RAM 31 may also be used to detect whether the chip element 13 is accurately attached between the terminals 12a and 12b.

As has been described earlier, the terminals 12a and 12b, the conductors 35a to 35c and the chip element 13 do not transmit light. Therefore, if the light from the first illuminating system 24 is received by the image sensor 22 and the second illuminating system 25 is not used, the chip element 13 may not be differentiated from the terminals 12a and 12b and the conductors 35a to 35c. However, according to the present invention, the second illuminating system 25 illuminates the terminals 12a and 12b which have been subjected to brushing. Since the intensity level of the reflected light from the abrasion scars 36 on the terminals 12a and 12b is higher than that of the chip element 13 and conductors 35a to 35c coated with the resist, these levels may be reliably discriminated from each other, thereby allowing easy discrimination of the presence of the chip element 13.

In the embodiment described above, the image signals are A/D converted before they are stored in the video memory 27. However, before such A/D conversion, the levels of these image signals may be compared by a comparator (not shown) with a reference signal of a level corresponding to the threshold level LT. Binary coding may thus be performed such that a signal of "1" is generated if the image signal level is higher than the threshold level LT and a signal of "0" is generated otherwise. In the above embodiment, only a second illuminating system 25 is used. However, a third illuminating system (not shown) may further be added symmetrically with respect to the second illuminating system 25 about a line normal to the plane of the printed circuit board 11. In this case, the abrasion scars 36 are illuminated from both sides.

Instead of moving the printed circuit board 11, the illuminating systems and the image sensor may be moved.

The system of the embodiment shown in FIG. 1 operates in synchronism with the output pulse from the sync signal generating circuit 23. However, a DC motor having a rotary encoder may be used in place of the pulse motor 17. In this case, the read/write control of the data from the image sensor 22 to the video memory 27 is performed on the basis of the output from the encoder.

In the embodiment described above, the light from the second illuminating system illuminates the abrasion scars perpendicularly. However, the present invention is not limited to this. If the amount of reflected light from the terminal conductors is significantly larger than that from the conductors coated with resist, these light components may be discriminated.

What we claim is:

1. An apparatus for detecting a position of an electronic part provided on one surface of a transparent printed circuit board, the electronic part being opaque and having an extremely low light reflection factor in comparison with that of a printed conductor provided on the printed circuit board, said apparatus comprising:
    an illuminating means for radiating light onto the printed circuit board so that a level of transmitted and reflected first light obtained from a surface of said electronic part is minimum in comparison with that obtained from a remainder of the printed circuit board, and so that a predetermined level difference occurs between said first light and a transmitted and reflected second light obtained from a surface of said printed circuit board on which no electronic part and printed conductor are provided;
    an image signal generating means responsive to a combination of the first and second light for generating an image signal of said printed circuit board; and
    means for checking if the electronic parts are correctly mounted in a predetermined position on the printed circuit board in accordance with said generated image signal.

2. An apparatus according to claim 1, wherein at least one pair of printed conductors each having a see-through hole are formed on one surface of said printed circuit board; a plurality of see-through holes corresponding to the holes of the conductors are formed in said printed circuit board; and said electronic part is mounted between said at least one pair of printed conductors used as terminals, and wherein said illuminating means includes first and second illuminating systems each comprising a light source lamp, a slit plate for converting light from said light source lamp into a thin light beam, and a cylindrical lens for converting the thin light beam into a parallel light beam.

3. An apparatus according to claim 2, wherein said image signal generating means comprises a linear image sensor for receiving the first and second light, and a timing signal generating circuit for generating clock signals for controlling a line scanning operation of said image sensor.

4. An apparatus according to claim 3, wherein said checking means comprises a microprocessor operative in response to the clock signals, and a RAM for storing the digital video data read out from a video memory by said microprocessor.

5. An apparatus according to claim 4, wherein said at least one pair of printed conductors, being used as terminals, formed on said one surface of said printed circuit board are connected to printed conductors being used as wiring conductors formed on said one surface of said printed circuit board, and wherein the digital video data stored in said RAM includes video data representing an intensity level of the transmitted light through said see-through holes formed on said terminals and said printed circuit board, and the video data is compared in level with corresponding data of a reference data read out from said video memory by said microprocessor.

6. An apparatus according to claim 1, wherein said printed circuit board has abrasion scars formed in a substantially uniform direction on said one surface of the board, and said illuminating means is provided for radiating a light which is inclined with respect to the surface of the printed circuit board and is substantially normal to the direction of the abrasion scars.

7. An examining apparatus for an electronic part provided on one surface of a transparent printed circuit board, the electronic part having an extremely low light transmission and reflection factor, compared with those of printed conductors on the printed circuit board, said apparatus comprising:

a first illuminating system for radiating first light onto the other surface of the printed circuit board to obtain transmitted light passed through the one surface of the printed circuit board;

a second illuminating system for radiating second light onto the one surface of said printed circuit board at a predetermined angle with respect to the one surface to obtain substantial reflected light in the same direction as that of the transmitted light;

image signal generating means responsive to a combination of the transmitted light and the reflected light from said printed circuit board to provide an image signal of said printed circuit board; and means for checking if the electronic part is correctly mounted in a predetermined position on the printed circuit board in accordance with the generated image signal.

8. An apparatus according to claim 7, wherein at least one pair of printed conductors each having see-through holes are formed on one surface of said printed circuit board; a plurality of see-through holes corresponding to the holes of the conductors are formed in said printed circuit board; and said electronic part is mounted between said at least one pair of printed conductors, used as terminals, and wherein each of said first and second illuminating systems comprises a light source lamp, a slit plate for converting light from said light source lamp into a thin light beam, and a cylindrical lens for converting the thin light beam into a parallel light beam.

9. An apparatus according to claim 8, wherein said image signal generating means comprises a linear image sensor for receiving the transmitted light and the reflected light, and a timing signal generating circuit for generating clock signals for controlling a line scanning operation of said image sensor.

10. An apparatus according to claim 9, wherein said checking means comprises a microprocessor operative in response to the clock signals, and a RAM for storing the digital video data read out from a video memory by said microprocessor.

11. An apparatus according to claim 10, wherein said at least one pair of printed conductors, being used as terminals, formed on said one surface of said printed circuit board is connected to printed conductors, being used as wiring conductors, formed on said one surface of said printed circuit board, and wherein the digital video data stored in said RAM includes video data representing an intensity level of the transmitted light through said see-through holes formed on said terminals and said printed circuit board, and the video data is compared in level with corresponding data of the reference data read out from said reference memory by said microprocessor.

12. An apparatus according to claim 7, wherein said printed circuit board has abrasion scars formed in a substantially uniform direction on said one surface of the board, and said second illuminating system is provided for radiating the second light substantially normal to the direction of the abrasion scars.

13. An examining apparatus for an electronic part provided on one surface of a transparent printed circuit board having abrasion scars formed in a substantially a uniform direction on said one surface of the board, the electronic part having an extremely low light transmission and reflection factor, compared with those of printed conductors on the printed circuit board, said apparatus comprising:

a first illuminating system for radiating first light onto the other surface of the printed circuit board to obtain a transmitted light passed through the one surface of the printed circuit board;

a second illuminating system for radiating second light onto said one surface of said printed circuit board, the second light being inclined at a predetermined angle with respect to the one surface and being substantially normal to the direction of the abrasion scars to obtain reflected light in substantially the same direction as that of the transmitted light;

image signal generating means responsive to a combination of the transmitted light and the reflected light from said printed circuit board to provide an image signal of said printed circuit board; and means for checking if the electronic part is correctly mounted in a predetermined position on the printed circuit board in accordance with the generated image signal.

14. A method for examining if an electronic part is correctly mounted at a predetermined position on a transparent or semi-transparent printed circuit board, comprising the steps of:

illuminating one surface of said printed circuit board to provide transmitted light passed through to the other surface thereof;

illuminating the other surface of said printed circuit board having an electronic part provided thereon to provide reflected light; and detecting the level of the combined transmitted and reflected light.

15. A method according to claim 14, wherein abrasion scars are formed on a surface of a printed conductor provided on the other surface of said printed circuit board, and the reflected light is obtained by illuminating said abrasion scars perpendicularly thereto.

16. A method according to claim 15, wherein the abrasion scars are illuminated by an incident light inclined with respect to the other surface of the printed circuit board so that the amount of the reflected light detected by the image sensor is maximum.

* * * * *

UNITED STATES PATENT AND TRADEMARK OFFICE
CERTIFICATE OF CORRECTION

PATENT NO. : 4,549,206
DATED : October 22, 1985
INVENTOR(S) : Etsuji Suzuki, Shimichi Uno, Kiyomu Chiyoda, Ryuhachirou Douji It is certified that error appears in the above-identified patent and that said Letters Patent is hereby corrected as shown below:

On the title page

Change "[73] Assignee: Tokyo Shibaura Denki Kabushiki Kaisha, Tokyo, Japan" to --[73] Assignee: Tokyo Shibaura Denki Kabushiki Kaisha, Kawasaki, Japan--.

Signed and Sealed this

Tenth Day of June 1986

[SEAL]

Attest:

Attesting Officer

DONALD J. QUIGG

Commissioner of Patents and Trademarks